United States Patent [19]
Williams et al.

[11] Patent Number: 4,950,911
[45] Date of Patent: Aug. 21, 1990

[54] APPARATUS AND METHOD FOR INSPECTING SHEET MATERIAL

[75] Inventors: Paul Williams, Columbus; Thomas M. Domin, Galena; Gary N. Burk, Columbus; Thomas O. McCanney, Sunbury; Steven M. Wilson, Grove City, all of Ohio

[73] Assignee: Process Automation Business, Inc., Columbus, Ohio

[21] Appl. No.: 299,723

[22] Filed: Jan. 19, 1989

Related U.S. Application Data

[63] Continuation-in-part of Ser. No. 171,208, Mar. 17, 1988, abandoned, which is a continuation of Ser. No. 940,139, Dec. 10, 1986, abandoned.

[51] Int. Cl.$^5$ ............................................. G01N 21/88
[52] U.S. Cl. ................................... 250/563; 250/572; 356/237
[58] Field of Search ........ 250/562, 563, 572, 235-236, 250/571, 559; 356/237, 429-431

[56] References Cited

U.S. PATENT DOCUMENTS

| | | | |
|---|---|---|---|
| 3,908,118 | 9/1975 | Micka | 250/572 |
| 4,378,494 | 3/1983 | Miller . | |
| 4,403,294 | 9/1983 | Hamada et al. | 250/562 |
| 4,417,149 | 11/1983 | Takeuchi et al. | 250/563 |
| 4,539,561 | 9/1985 | Wulff . | |
| 4,675,730 | 6/1987 | Adomaitis et al. . | |
| 4,685,139 | 8/1987 | Masud et al. | 250/562 |
| 4,724,481 | 2/1988 | Nishioka . | |

Primary Examiner—David C. Nelms
Attorney, Agent, or Firm—Killworth, Gottman, Hagan & Schaeff

[57] ABSTRACT

Apparatus for inspecting sheet material having known characteristics is disclosed. The apparatus comprises means for providing a plurality of pixel signals each having a magnitude representing the intensity of electromagnetic radiation received from a corresponding point on the sheet material. The apparatus also comprises signal processing means for comparing the magnitude of each one of the pixel signals to a corresponding reference range defined by the known characteristics of the sheet material and generating a characteristic signal. The characteristic signal includes an event signal for each of the magnitudes falling outside of the corresponding reference range and a data signal for each of the magnitudes falling within the range, wherein the data signal represents the magnitude of the pixel signal. The signal processing means also generates an address signal representing the point on the sheet material at which the characteristic signal is generated. The apparatus also comprises system processing means for storing the event signals and the corresponding address signals to provide an indication of deviation from the known characteristics of the sheet material.

49 Claims, 7 Drawing Sheets

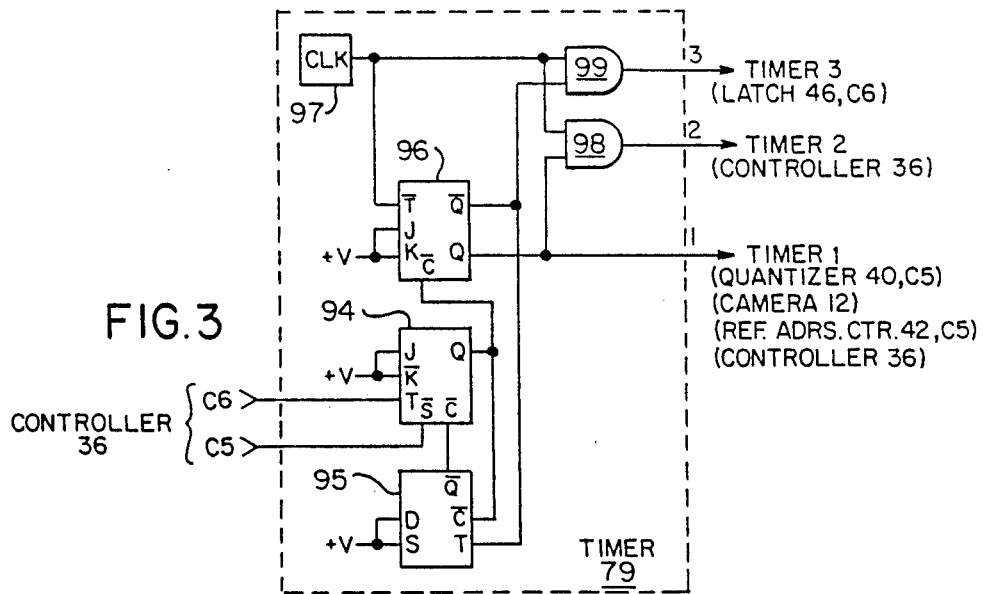
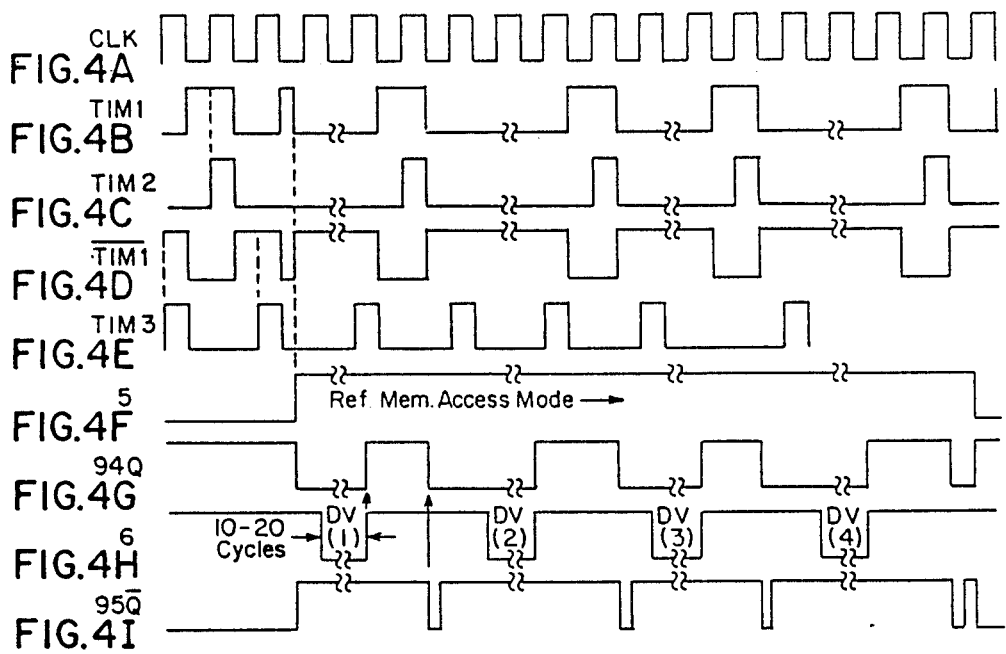

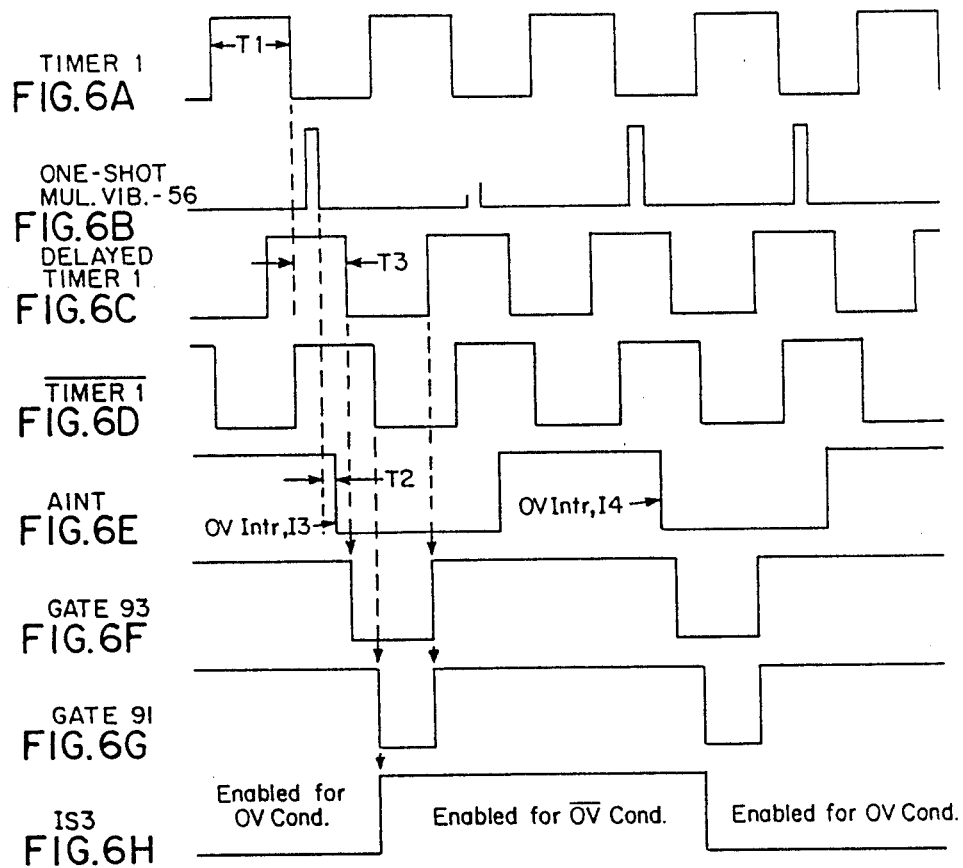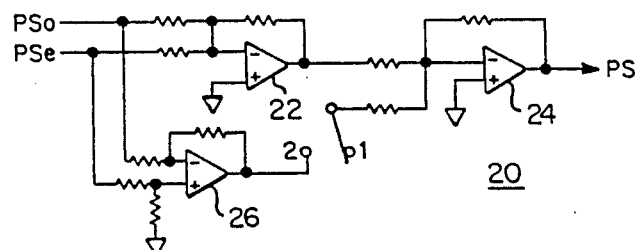

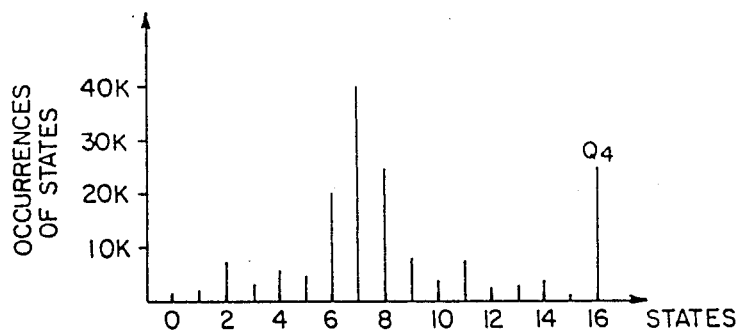
FIG. 9 : HISTOGRAM OF CHARACTERISTIC SIGNALS (CS)
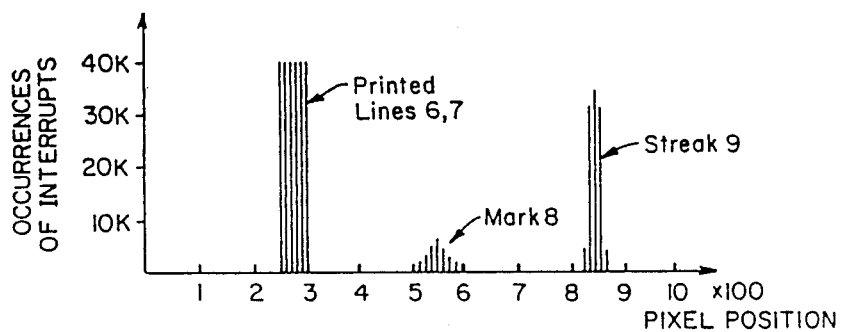
FIG. 10 : HISTOGRAM OF INTERRUPT SIGNALS (I)
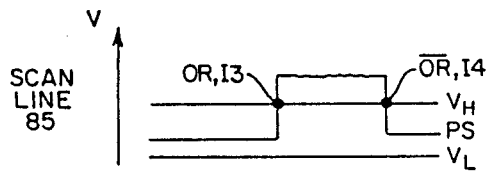
FIG. 11A
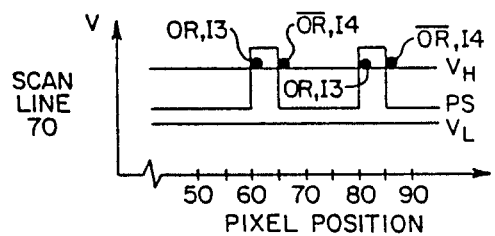
FIG. 11B
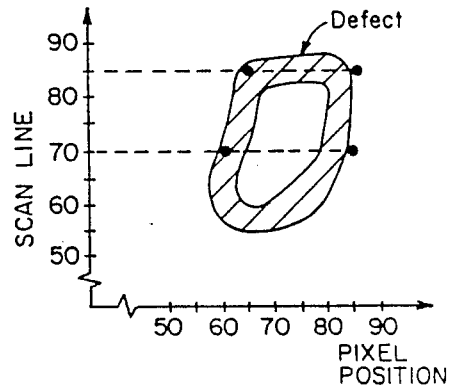
FIG. 12 : TOPOGRAM OF INTERRUPTS

APPARATUS AND METHOD FOR INSPECTING SHEET MATERIAL

This application is a continuation-in-part of Application Ser. No. 171,208 filed Mar. 17, 1988, now abandoned which is a continuation of application Ser. No. 940,139 filed Dec. 10, 1986, now abandoned.

BACKGROUND OF THE INVENTION

The present invention relates to the inspection of sheet material and, more particularly, to apparatus and method for inspecting sheet material having known characteristics.

Optical scanners have been used to inspect sheet material moving as a continuous web in a high-speed production line at rates up to several hundred meters per minute. The material can be, for example, paper, plastic, or metal. Such scanners may be set up to inspect the material for any number of characteristics measured by illuminating the material and comparing the intensity reflected or transmitted therefrom with a threshold model defined by already known or learned characteristics. The optical scanners include an array of photosites, each providing a pixel signal having a magnitude representing the intensity of light received from a corresponding point on the sheet material. Each photosite corresponds to the location of the point on the sheet material being inspected. The length of the array corresponds to the width of the sheet material so that the photosites provide successive sets of pixel signals, each set corresponding to a scan of the width of the sheet material.

As quality requirements have become more demanding, it has become desirable to inspect 100% of the sheet material rather than taking a sample. High-speed optical cameras are capable of providing pixel signals at rates up to 20 million per second. Thus, if an optical camera has a linear array of 1,000 photosites for scanning the width of the sheet material, it would provide about 20,000 scans per second which is more than sufficient to provide 100% sheet inspection on high-speed production lines. Although such cameras are currently available, economically-priced equipment for processing the pixel signals provided at the same high data speeds currently is unavailable.

Furthermore, even if such processing equipment were available, it is not necessary to process all of the pixel signals because only the deviations from the threshold model are important and typically represent only a small portion of the pixel signals being measured. It is more desirable to measure all of the pixel signals and process only those which represent a deviation from the threshold model, processing equipment would extract and store only that data which is significant, i.e., data indicating a deviation from the threshold model. Thus, it also becomes necessary to accurately define the threshold model to insure that most of the significant data is actually extracted from the stream of pixel signals being generated by the optical scanner.

Accordingly, there is a need for a method and apparatus for inspecting sheet material having known characteristics by comparing all of the pixel signals to a threshold model to accomplish 100% inspection of the sheet material, while extracting and storing only significant data from the stream of pixel signals and accurately defining and adjusting the threshold model to ensure that most of the significant data is extracted.

SUMMARY OF THE INVENTION

The present invention meets this need by providing apparatus for inspecting sheet material having known characteristics. The apparatus comprises means for providing a plurality of pixel signals, each having a magnitude representing the intensity of electromagnetic radiation received from a corresponding point on the sheet material. The apparatus further comprises signal processing means, responsive to the means for providing a plurality of pixel signals, for comparing the magnitude of each one of the pixel signals to a corresponding reference range defined by the known characteristics of the sheet material, the reference range being the threshold model. The signal processing means then generates a characteristic signal, an event signal for each of the magnitudes falling outside of the corresponding reference range and a data signal for each of the magnitudes falling within the reference range, the data signal representing the magnitude of the pixel signal, and an address signal representing the point on the sheet material at which the characteristic signal is generated. The apparatus further comprises system processing means, responsive to the signal processing means, for storing the event signals and the corresponding address signals to provide an indication of deviation from the known characteristics of the sheet material.

The means for providing a plurality of pixel signals includes an array of photosites, each providing one of the pixel signals. The address signals each represent the position of a photosite in the array corresponding to the location of the point on the sheet material at which the characteristic signal is generated. The length of the array corresponds to the width of the sheet material so that the photosites provide successive sets of pixel signals, each set corresponding to a scan of the width of the sheet material. The signal processing means includes control means, responsive to the system processing means, for providing an end-of-scan signal when the array provides a full set of pixel signals, and wherein the system processing means, responsive to the end-of-scan signals, provides a histogram of the occurrences of the event signals at each photosite position for a predetermined number of scans. The characteristic signals are n-bit digital signals and wherein the system processing means provides a histogram of the occurrences of the states of the digital signals.

The signal processing means might further include reference means, responsive to the system processing means, for storing a high and low reference value for each of the reference ranges, wherein the high and low reference values are derived in response to the known characteristics of the sheet material and are provided to define each of the reference ranges between a high threshold and a low threshold for comparison to the magnitude of the pixel signals. The signal processing means further includes converter means, responsive to the system processing means, for reading and storing the data signals and the corresponding address signals, the system processing means reading the signals from the converter means, adding a high factor to each of the data signals to determine the high reference value, subtracting a low factor from each of the data signals to determine the corresponding low reference value, and storing the high and low reference values in the reference means for defining new reference ranges for comparison to the magnitude of subsequent pixel signals.

The signal processing means further includes control means, responsive to the system processing means, for providing an overrange interrupt signal when the event signal is generated because the magnitude of the pixel signal is greater than the high threshold and an underrange interrupt signal when the event signal is generated because the magnitude of the pixel signal is less than the low threshold. The control means generates a not overrange signal when the magnitude of a pixel signal is less than the high threshold. The control means also generates a not underrange signal when the magnitude of a pixel signal is greater than the low threshold.

The present invention further meets this need by providing a method for inspecting sheet material having known characteristics. The method comprises the steps of providing a plurality of pixel signals, each having a magnitude representing the intensity of electromagnetic radiation received from a corresponding point on the sheet material and comparing the magnitude of each one of the pixel signals to a corresponding reference range defined by the known characteristics of the sheet material. The method also comprises the steps of generating a characteristic signal, an event signal for each of the magnitudes falling outside of the corresponding reference range and a data signal for each of the magnitudes falling within the range, the data signal representing the magnitude of the pixel signal and generating an address signal representing the point on the sheet material at which the characteristic signal is generated. The method then includes the step of storing the event signals and the corresponding address signals to provide an indication of deviation from the known characteristics of the sheet material.

The method may also comprise the steps of deriving a high and low reference value for each of the reference ranges in response to the known characteristics of the sheet material, storing the high and low reference values and providing the high and low reference values to define each of the reference ranges between a high threshold and a low threshold for comparison to the magnitude of the pixel signals. The method further includes steps of storing the data signals and the corresponding address signals, adding a high factor to each of the data signals to determine the high reference value, subtracting a low factor from each of the data signals to determine the corresponding low reference value, and storing the high and low reference values for defining new reference ranges for comparison to the magnitude of subsequent pixel signals.

The method may further comprise steps of providing an overrange interrupt signal when the magnitude of the pixel signal is greater than the high threshold and providing an underrange interrupt signal when the magnitude of the pixel signal is less than the low threshold. The method may further include a step of generating a not overrange interrupt signal when the magnitude of a pixel signal is less than the high threshold. The method may also include the step of generating a not underrange interrupt signal when the magnitude of a pixel signal is greater than the low threshold.

Accordingly, it is an object of the present invention to provide apparatus and method for measuring all of the pixel signals to accomplish 100% inspection of the sheet material while extracting and storing onl significant data from the stream of pixel signals provided by the optical camera; to provide apparatus and method for storing only a portion of the pixel signals to define and continually adjust the threshold model to which subsequent pixel signals are compared; and to provide apparatus and method for providing a graphical representation of the deviations from the threshold model. Other objects and advantages of the invention will be apparent from the following description, the accompanying drawings, and the appended claims.

BRIEF DESCRIPTION OF THE DRAWINGS

FIG. 3 is an electrical schematic of a timer shown as a block in FIG. 2;

FIGS. 4A, 4B, 4C, 4D, 4E, 4F, 4G, 4H, and 4I are a series of time graphs illustrating the relative timing sequence of signals existing within the timer of FIG. 3;

FIGS. 6A, 6B, 6C, 6D, 6E, 6F, 6G, 6H are series of time graphs illustrating the relative timing sequence of signals existing within the controller of FIG. 2;

FIG. 7 is an electrical schematic of a preprocessor for the camera shown in FIG. 1;

FIG. 9 is a histogram of the grey scale of the characteristic signals CS;

FIG. 10 is a histogram of the interrupt signals;

FIG. 11 is a graph showing the relative magnitudes of the pixel signals and the reference range in conjunction with various interrupt signals I; and FIG. 12 is a topogram of the interrupt signals I for a plurality of camera scans.

DETAILED DESCRIPTION OF THE PREFERRED EMBODIMENTS

Figures 1, 1A:
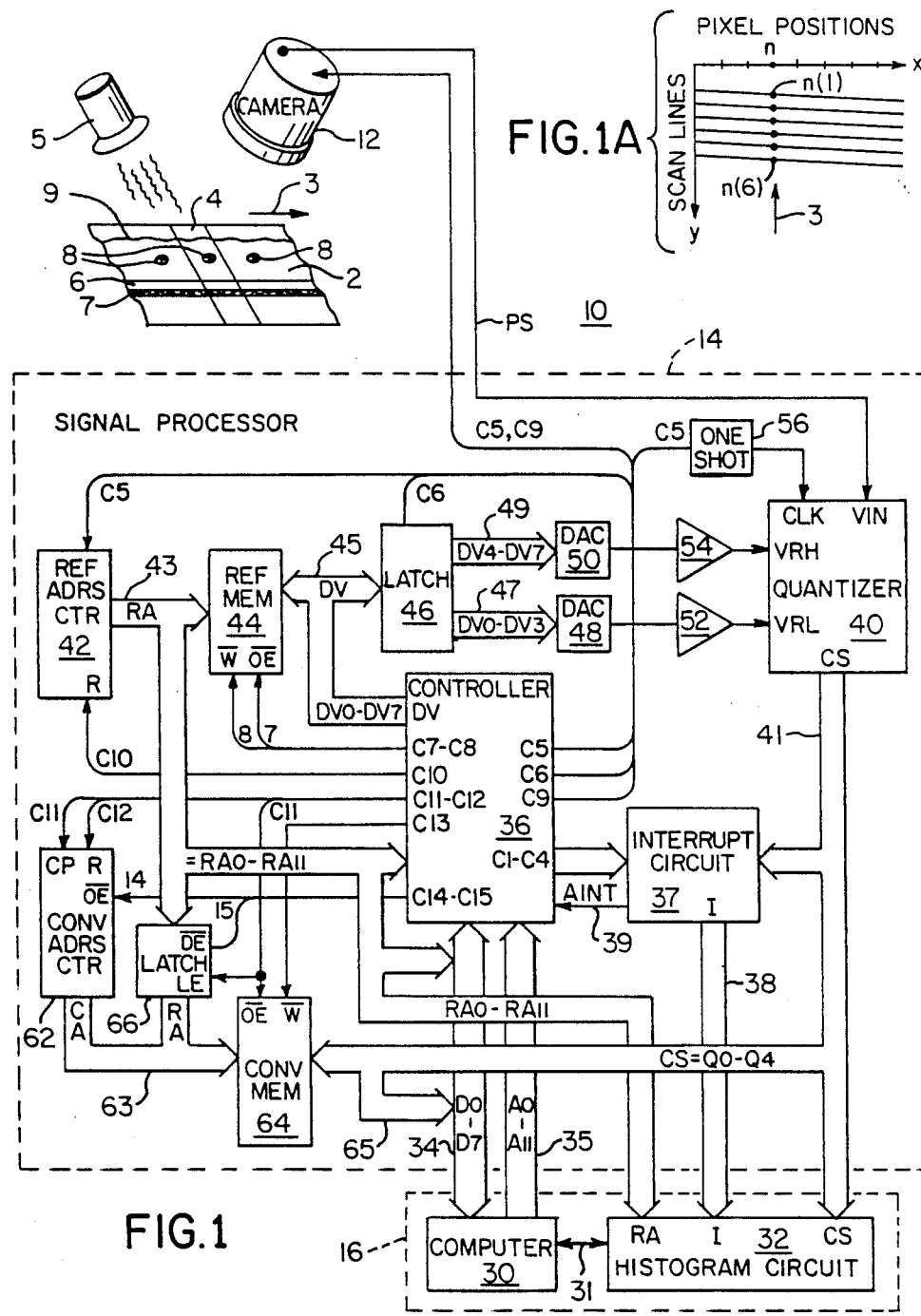
FIG. 1 is an electrical schematic of the apparatus for inspecting sheet material according to the present invention which comprises a camera and a signal processor which includes a controller and an interrupt circuit.
FIG. 1A is a graph showing the scanning pattern of the camera shown in FIG. 1.

Referring to FIG. 1. apparatus for inspecting sheet material is indicated generally at 10 and comprises a camera 12 for providing a plurality of pixel signals PS, a signal processor 14 for receiving pixel signals PS from camera 12, and a system processor 16 connected to the signal processor 14. Camera 12 is positioned to view a web of sheet material 2 moving in the direction on a production line (not shown) indicated by an arrow 3. Sheet material 2 can be, for example, paper, plastic. steel or any other material capable of being inspected. Camera 12 views a portion of sheet material 2, an inspection area 4, which is illuminated by a source of light 5 of known intensity. It is to be understood, that source of light 5 can be any source of electromagnetic radiation, whether or not visible, that can be altered by the sheet material being inspected and measured by an appropriate sensor. As such, the present invention is not to be limited by the type of source or sensors being used, even though the term "light" is used herein.

Camera 12 provides pixel signals PS that are analog signals having a magnitude corresponding to the reflected intensity of light received from a corresponding point on sheet material 2 as shown. It is to be understood, however, that source of light 5 can be positioned to illuminate the opposite side of sheet material 2, so that camera 12 provides pixel signals pS having a magnitude corresponding to the transmitted intensity of light received. Thus, apparatus 10 can be used to inspect sheet material for any number of characteristics related to physical properties of the sheet material or flaws in the sheet material. Furthermore, apparatus 10 can identify such characteristics regardless of variations in the intensity of light provided by the source of light, regardless of variations in the sensitivity of the camera, and regardless of variations in the sheet material such as, for example, embossed patterns or printing 6. 7 on the surface of sheet material 2. Such features will be described below in more detail.

Camera 12 comprises an array of photosites (which can be, for example, charge-coupled devices) that is arranged as a linear array (not shown). Such cameras are available from the Fairchild Camera and Instrument Corporation. As mentioned above, each photosite provides one pixel signal PS, the magnitude of which corresponds to the intensity of light from a corresponding small area or point on sheet material 2. The linear array is aligned in a direction generally transverse to the direction 3 that sheet material 2 moves on the production line and is focused on the width of sheet material 2 so that the photosites provide successive sets of pixel signals PS. As a result, each set of pixel signals PS corresponds to a scan of the width of sheet material 2 or scan line as shown generally in FIG. 1A. A single photosite, provides a pixel signal PS for each scan corresponding to a series of points extending longitudinally along sheet material 2, for example at points n(1) to n(6).

Depending on the width of sheet material 2, several cameras can be electrically coupled and their photosites coaxially aligned to provide a sufficient number of photosites in the linear array. In the present embodiment, the linear array consists of 1,024 photosites. Thus, if camera 12 provides pixel signals PS at the rate of 20 million per second, it will provide approximately 20,000 scan lines per second. Storing all of the pixel signals PS received from one photosite over a period of three seconds would require 64K of memory. It is to be understood, however, that a camera having a two-dimensional photosite array can be used as well. Successive rows of photosites in a two-dimensional array would be scanned and the pixel signals PS would still be provided to signal processor 14 as a serial stream of analog data.

Camera 12 is also equipped with two other serial outputs (not shown). one of which provides a stream of even pixel signals $PS_e$ from the evenly numbered photosites and the other which provides a stream of odd pixel signals $PS_o$ from the odd numbered photosites. These signals are applied to a preprocessor indicated generally at 20 in FIG. 7 which can also be used to provide a plurality of pixel signals PS to the signal processor 14, wherein successive pairs of photosites each provide one pixel signal PS. Thus, each pixel signal has a magnitude representing the intensity of light received from a corresponding point on the sheet material as measured by both photosites.

In a first embodiment of preprocessor 20, successive even and odd pixel signals, $PS_e$ and $PS_o$, are summed by an operational amplifier 22 configured as an adding circuit. The sum is inverted by another operational amplifier 24, also configured as an adding circuit, which provides the pixel signal PS at its output. In a second embodiment, the successive even and odd pixel signals. $PS_e$ and $PS_o$ are also subtracted by an operational amplifier 26 configured as a subtracting circuit. The difference at the output of the operational amplifier 26 is applied through a closed switch 28, when switched to position 2 from position 1, to the input of operational amplifier 24. As a result, the pixel signal PS at the output of operational amplifier 24 is equal to the summation of the sum of the even and odd pixel signals and the difference between the odd and even pixel signals, preprocessing the even and odd pixel signals, $PS_e$ and $PS_o$, by using either embodiment improves the signal to noise ratio and enhances the edges of flaws without a significant loss of information. The flaws will be discussed below in detail.

System processor 16 comprises a computer 30 and histogram circuit 32 connected to the computer 30 by a bidirectional bus 31. Computer 30 is connected to an 8-bit bidirectional system data bus 34 and provides a 12-bit address signal, $A_0$ to $A_{11}$, on a bus 35. The signal processor 14 comprises control means including a controller 36 and an interrupt circuit 37. Interrupt circuit 37 provides interrupt signals I, $I_1$ to $I_4$, to histogram circuit 32 via a bus 38 and an Any Interrupt signal AINT to controller 36 via a wire 39. Both controller 36 and interrupt circuit 37 will be discussed below in more detail.

The signal processor 14 further comprises a quantizer 40 for receiving the pixel signals PS from camera 12 at input VIN. Quantizer 40 is a high-speed, analog-to-digital converter that compares the magnitude of each pixel signal PS to a corresponding reference range. A high reference value VRH and a low reference value VRL are inputed to quantizer 40 to define the reference range between a high threshold VH and a low threshold VL within quantizer 40. Quantizer 40 provides a digital output signal, a characteristic signal CS, for each pixel signal PS being compared. Each characteristic signal CS includes either a data signal DS or an event signal ES. Quantizer 40 provides an event signal ES when the magnitude of the compared pixel signal PS falls outside the corresponding reference range and a data signal DS when the magnitude falls within the reference range.

In the present embodiment, the data signal DS is 4-bit digital signal. $Q_0$ to $Q_3$ which expresses the magnitude of the pixel signal PS in one of 15 states. The event signal ES is a 1-bit digital signal, $Q_4$, being the fifth bit of the characteristic signal CS, or the least significant state of the data signal $D_0$ where to $Q_4$ are all low. When the magnitude of the pixel signal PS is greater than the reference range or the high threshold VH, the event signal ES where $Q_4$ is high indicates the occurrence of an overrange, OR, event. When the magnitude of the pixel signal PS is less than the reference range or the low threshold VL, the event signal ES where $Q_0$–$Q_4$ all low indicates the occurrence of an underrange, UR. event. Quantizer 40 is model number AM6688 supplied by Advanced Micro Devices. Model number MCI0319 is a similar device available from Motorola that can also be used. The characteristic signals CS are provided to histogram circuit 32 and interrupt circuit 37 via a bus 41.

The signal processor 14 also comprises reference means which includes a reference address counter 42, a reference memory 44, a latch 46, a pair of digital-to-analog converters or DACS 48 and 50, and a pair of operational amplifiers 52 and 54. The reference counter 42 provides a 12-bit reference address signal RA, $RA_O$ to $RA_{11}$, to reference memory 44, controller 36, system data bus 34, and histogram circuit 32 via a bus 43. The reference address signal RA represents the point on the sheet material from which the pixel signal PS is generated and one is provided for each characteristic signal CS. The reference address counter 42 has an inverted reset input R which is connected to output C10 from controller 36. Reference memory 44 is a combination of conventional static RAM or a combination of several static RAMS necessary to provide enough addressable memory for storing information corresponding to a set of pixel signals. Reference memory 44 has an inverted write input W and an inverted output enable input OE which are connected to outputs C8 and C7, respectively, from controller 36.

Reference memory 44 scores a plurality of reference values DV, which are formed by an 8-bit signal $DV_0$–$DV_7$ in the present embodiment. The high reference value VRH and the low reference value VRL are the most significant and least significant 4-bit words, respectively, of the reference value DV, $DV_0$–$DV_7$, and are provided to the input of latch 46 via a bidirectional bus 45. Latch 46 provides the low reference value VRL, the least significant half of the reference value DV. $DV_0$ to $DV_3$, to DAC 48 and the high reference value VRH, the most significant half of the reference value. $DV_4$ to $DV_7$ to DAC 58 via buses 47 and 49. respectively. The output of each DAC 48, 50 provides an analog current signal which is converted to an analog voltage by operational amplifiers 52 and 54, respectively, to generate the low and high reference values, VRL and VRH, that define the reference range for quantizer 40.

Signal processor 14 finally comprises converter means which includes a converter address counter 62, a converter memory 64 and a latch 66. The converter address counter 62 provides a 12-bit converter address signal CA to converter memory 64 on a bus 63. Converter address counter 62 has a clock input CP, a reset input R and an inverted output enable input OE which are connected to outputs C11, C12, and C14, respectively, from controller 36. Latch 66 provides the reference address signal RA to converter memory 64 on the same bus 63 and has its latch enable LE input and its inverted output enable input 0E connected to outputs C11 and C15, respectively, of controller 36. Converter memory 64 is also a static RAM having the same memory requirements as reference memory 44. The data terminals of converter memory 64 are connected to quantizer 40 via bus 41 and to system data bus 34 via bus 65. Outputs C13 and C11 of controller 36 are connected to the inverted write input W and the inverted output enable OE, respectively, of converter memory 64.

Figure 2:
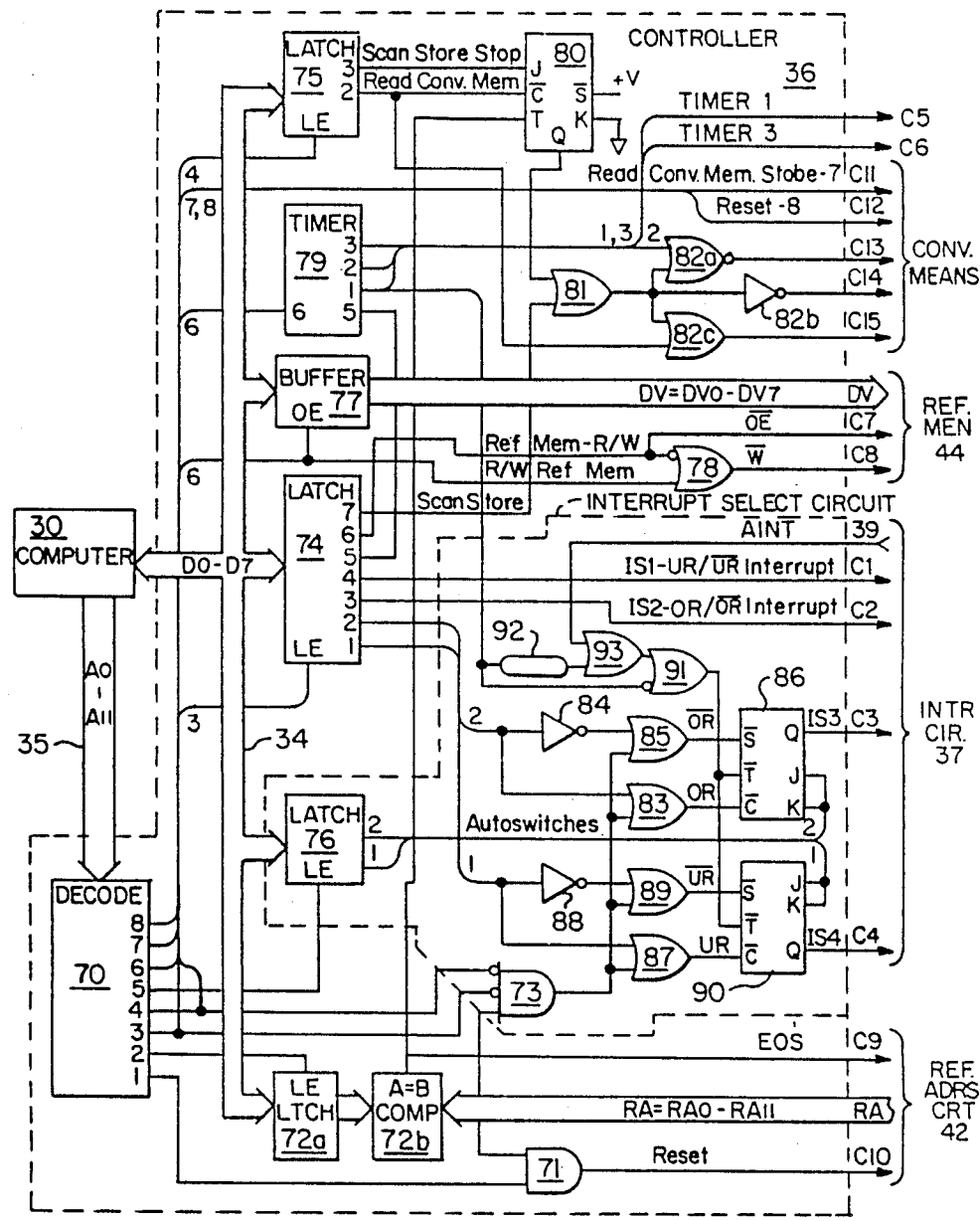
FIG. 2 is an electrical schematic of the controller shown as a block in FIG. 1.

Referring to FIG. 1 and in more detail to FIG. 2, controller 36 provides a timing signal. TIMER 1 from its output C5 to the clock inputs of quantizer 40 via a one-shot multi-vibrator 56, reference address counter 42, and camera 12. Controller 36 provides a second timing signal. TIMER 3, from its output C6 to the clock input of latch 46. Controller 36 comprises a one-of-eight decoder 70 which is addressed by computer 30 to provide eight discrete control outputs 1 to 8. Control output 1 is connected to the first input of an AND gate 71 to enable a reset signal via output C10 to reference address counter 42. Control output 2 is connected to the enable input of a latch 72a which provides a digital output to a comparator 72b. Control output 3 is connected to the first inverted input of an AND gate 73 and the enable input of a latch 74. Control output 4 is connected to the second inverted input of AND gate 73 and to the enable input of a latch 75. Control output 5 is connected to the enable input of a latch 76. Control output 6 is connected to the enable input of a buffer 77, the first input of an OR gate 78, and input 6 of a timer 79. Finally, control outputs 7 and 8 are provided at outputs C11 and C12 as described above. Computer 30 is connected by the bidirectional system data bus 34 to latches 71, 74, 75 and 76, and buffer 77. Computer 30 operates controller 36 through decoder 70 and the system data bus 34 pursuant to a set of instructions provided by a program that will be described below in more detail when referring to the modes of operation.

Outputs 2 and 3 of latch 75 are connected to the inverted clear input and the J input, respectively, of JK flip-flop 80, the noninverting output of which is connected to the first input of an OR gate 81. The output of OR gate 81 is connected to the first input of an OR gate 82a. the inverted output of which provided as output C13, an inverter 82b, the output of which is provided as output C14, and the first input of an OR gate 82c, the output of which is provided as output C15. Output 2 of latch 75 is also connected to the second input of OR gate 82c. Output bit 2 of latch 74 is provided to the first input of an OR gate 83 and through an inverter 84 to the first input of another OR gate 85. The outputs of OR gate 83 and 85 are connected to the inverted clear and set inputs, respectively, of a JK flip-flop 86, the noninverting output of which is provided as output C3 to interrupt circuit 37. Output bit 1 is connected to the first input of an OR gate 87 and through an inverter 88 to the first input of an OR gate 89. The outputs of the OR gates 87 and 89 are connected to the inverted clear and set inputs, respectively, of a JK flip-flop 90, the noninverting output of which is provided as output C4 to interrupt circuit 37. Finally, output 1 from timer 79 is connected to the first input of an OR gate 91, an inverted input, and through a time delay element 92 to the first input of an OR gate 93. The output of OR gate 91 is connected to the inverted toggle inputs of JK flip-flops 86 and 90. Having described all the components in FIG. 2, the remaining connections are as shown in the drawings.

Referring in more detail to FIG. 3, control output 6 from decoder 70 and output bit 5 from latch 74 are connected to the toggle input and the inverted set input, respectively, of a JK flip-flop 94, the J and K inputs being biased as shown. The noninverting output of JK flip-flop 94 is connected t the inverted clear inputs a D-type flip-flop 95 and a JK flip-flop 96, which is toggled by a clock 97. The noninverting output of JK flip-flop 96 provides the TIMER 1 signal at output 1 and is connected to the first input of an AND gate 98, the output of which provides the TIMER 2 signal at output 2. The inverting output of JK flip-flop 96 is connected to the toggle input of flip-flop 95 and the first input of an AND gate 99 which provides the TIMER 3 signal at output 3. Clock 97 is also connected to the second inputs of AND gates 98 and 99. The inverting output of flip-flop 95 is connected to the inverted clear input of JK flip-flop 94.

Referring to FIGS. 3 and 4, the clock signal can be provided at a frequency up to 20 MHz. Since JK flip-flop 96 changes its state in response to a negative-going edge of the clock signal, the frequency of the TIMER 1 is half that of the clock signal. The TIMER 2 signal is the logical sum of the TIMER 1 signal and the clock signal, and the TIMER 3 signal is the logical sum of the inverted TIMER 1 signal and the clock as shown. Output bit 5 of latch 74 is normally low, but goes high to enable a reference memory access mode which will be described below in more detail. When output bit 5 goes high, the positive level on the set input of flip-flop 94 allows its noninverting output to go low. When this noninverting output goes low, the TIMER 1 signal goes low and the inverted output of flip-flop 95 goes high. When output bit 5 goes high it enables write access to reference memory 44.

Control output 6 is normally high but goes low to write the reference value DV from computer 30 to reference memory 44. Control output 6 remains low for a period of time unrelated to the clocking while the reference value DV is being written into reference memory 44, as indicated by the break in all of the time lines. After the reference value DV has been written into reference memory 44, control output 6 goes high. This positive going edge causes flip-flop 94 to change states so that its noninverting output goes high to enable the TIMER 1 signal on the next negative-going edge of the clock signal. When the TIMER 1 goes low, the inverted TIMER 1 signal goes high so that the positive-going edge changes the state of flip-flop 29. As a result, the inverted output of flip-flop 29 goes low clearing flip-flop 94 so that its noninverting output also goes low. The low signal from flip-flop 94 clears flip-flop 95 so that its inverted output goes back high and prevents flip-flop 96 from toggling. The purpose of this circuit is to increment reference address counter 42 for each reference memory write cycle that occurs as will be discussed below in more detail. This cycle repeats as long as the reference memory access signal, output bit 5, is enabled while reference values, DV(2) to DV(4), are being written into reference memory 44.

Figure 5:
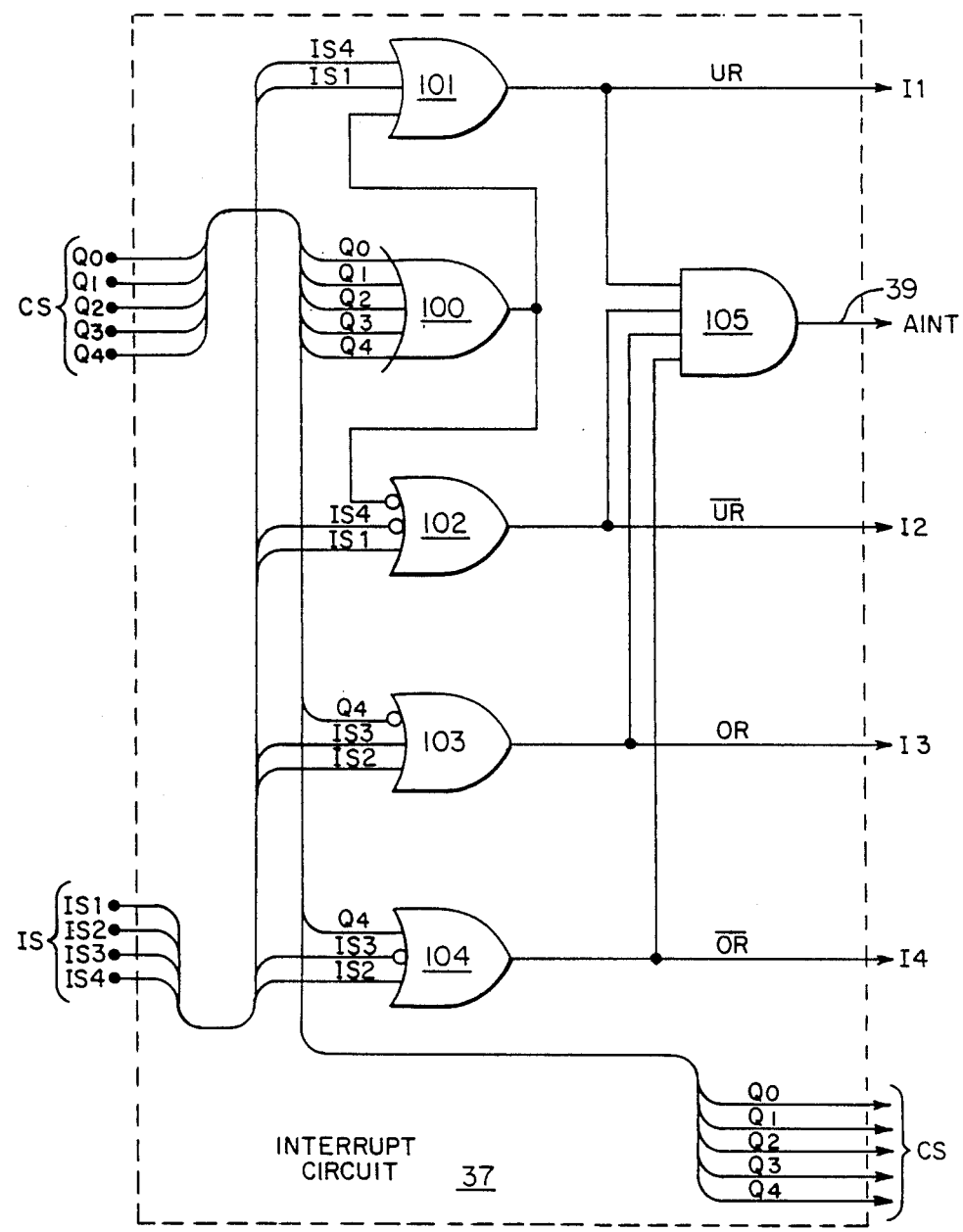
FIG. 5 is an electrical schematic of the interrupt circuit shown as a block in FIG. 1 and providing interrupt signals I, $I_1$–$I_4$. and characteristic signals, CS, in accordance with the present invention.

Referring to FIG. 5, interrupt circuit 37 comprises five OR gates 100-104 and an AND gate 105. Bus 41 connects the characteristic signals CS, Q0 to Q4, to interrupt circuit 37 and inputs all of the signals to the five separate inputs of gate 100. The output of gate 100 is connected to the first input of OR gate 101 and an inverted input of gate 102. The digital signal at Q4 is provided to the inverted input of gate 103 and the first input of gate 104. The output of gates 101 to 104 provide the interrupt signals I, $I_1$ to $I_4$, as outputs and are also connected to the inputs of AND gate 105. The outputs gates 101-104 are normally high and provide an interrupt signal I when going low. Thus, the occurrence of any interrupt signal, $I_1$ to $I_4$, drives the normally high output of AND gate 105 low to provide the Any Interrupt signal, AINT, referred to above.

Controller 36 provides four Interrupt Select (IS) signals, IS1 to IS4, from outputs Cl to C4, respectively, which are connected to OR gates 101 to 104 as shown in FIG. 5. Combinations of the IS signals are used to enable interrupt circuit 37 to generate one or more of the interrupt signals, I1 to I4, in response to a detected event signal ES. The combinations of IS signals necessary to enable an interrupt signal I are summarized as follows:

1. If IS1 and IS4 are low, interrupt circuit 37 is enabled to detect an UR event and provide an UR interrupt signal. Il. i.e.. enabled for an UR condition;
2. If IS1 is low and IS4 is high, interrupt circuit 37 is enabled to detect an UR event and generate a not UR interrupt signal, I2, i.e., enabled for a not UR condition:
3. If IS2 and IS3 are low, interrupt circuit 37 is enabled to detect an OR event and provide an OR interrupt signal, I3, i.e., enabled for an OR condition; and
4. If IS2 is low and IS3 is high, interrupt circuit 37 is enabled to detect an OR event and generate a not OR interrupt signal, I4, i.e.. enabled for a not OR condition.

For example, when it becomes desirable to generate an OR interrupt, I3, interrupt circuit 37 is enabled for an OR condition by setting IS2 and IS3 low so that the output of gate 103 goes low to provide the OR interrupt signal I3 when Q4 goes high as the result of the magnitude of the pixel signal exceeding the high threshold VH. Correspondingly, when it becomes desirable to generate a not OR interrupt, I4, interrupt circuit 37 is enabled for a not OR condition by setting IS2 low and IS3 high so that the output of gate 104 goes low to provide the not 0R interrupt signal I4 when Q4 goes low as the result of the magnitude of the pixel signal dropping below the high threshold VH. The circuitry that provides the interrupt select signals IS, an interrupt select circuit, will be described below.

In operation, apparatus 10 can be used in several modes such as, for example, a scan store operation mode, a converter memory access mode, a reference memory access mode, an inspection mode and an interrupt mode. In the "scan store mode", quantizer 40 transmits characteristic signals CS to converter memory 64. To accomplish this, computer 30 is programmed so that bit 7 of control output 3, the scan store signal, and bit 2 of control output 4, the read converter memory enable signal, both go low and. as such, are enabled. When bit 2 goes low, the noninverted output of flip-flop 80 goes low and, along with the low scan store signal, causes the output of gate 81 to go low. When the output of gate 81 goes low, it turns on gate 82a which enables the TIMER 2 signal to be clocked through at output C13 to converter memory 64 which is enabled thereby to store the characteristic signals CS. Control output 7, the read converter memory signal, also goes low and is connected through output C11 to converter memory 64 to strobe the characteristic signals CS from quantizer 40, and a portion of the corresponding address, to converter memory 64 at the address specified by reference address counter 42 through bus 43 and latch 66. In the "converter memory access" mode, the characteristic signals CS stored in converter memory 64 are transferred to computer 30. To accomplish this, computer 30 is programmed so that bit 7 of control output 3, the scan store signal, goes high and bit 2 of control output 4 goes low to disable the scan store mode and reset flip-flop 80. Computer 30 is also programmed so that control output 8 goes high to reset converter address counter 62 via output C12. When the scan store signal goes high, it is provided through gate 81 and inverter 82b as output C14 to enable converter address counter 62 which controls the address from which computer 30 will read the characteristic signals CS from converter memory 64. Control output 7 then strobes the characteristic signals CS, and the stored portion of the reference address RA. from converter memory 64 to computer 30 via data bus 65 and system data bus 34.

In the "reference memory access" mode, the high and low reference values. VRH and VRL, are transferred from computer 30 to reference memory 44. To accomplish this, computer 30 is programmed to first convert the data signals DS for a given pixel position to a corresponding pair of reference values, VRH and VRL, as will be described below in more detail. Computer 30 is then programmed so that bit 5 of control output 3, the reference memory access signal, goes high and is provided to timer 79 to stop inspection processing and to enable write access to reference memory 44 as described above with respect to timer 79 as shown in FIGS. 3 and 4. Computer 30 is also programmed so that bit 6 of control output 3 provides a high signal at output C7 to enable write access to reference memory 44, i.e., disabling the output-enable input OE. This high signal at bit 6 is also provided at the inverting input of gate 78 so that the reference values. VRH and VRL, are transmitted from computer 30 to reference memory 44. Computer 30 is finally programmed so that control output 6, the R/W reference memory signal, goes low to drive the output of gate 78 low. This low output is provided at output C8 to enable the reference values DV to be written from computer 30 to reference memory 44 via buses 34 and 45. The R/W reference memory signal actually strobes the reference values DV from computer 30 into reference memory 44 and increments reference address counter 42 by one count through timer 79 as described above.

These three modes can then be used to perform various functions related to initializing signal processor 14 and computing and adjusting the reference range for each pixel signal PS. The signal processor 14 is initialized to compensate for the varying light intensity from source 5, variations in the sensitivities of the photosites of camera 12 and the variations in sheet material 2 as described above. To normalize these variations, the following procedure is used.

Figure 8A:
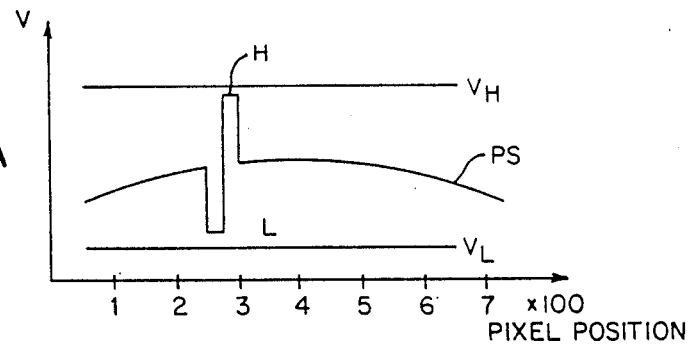
FIGS. 8A to 8D are graphs showing the relative magnitudes of the pixel signals and the reference range for one camera scan according to the present invention.
Figure 8B:
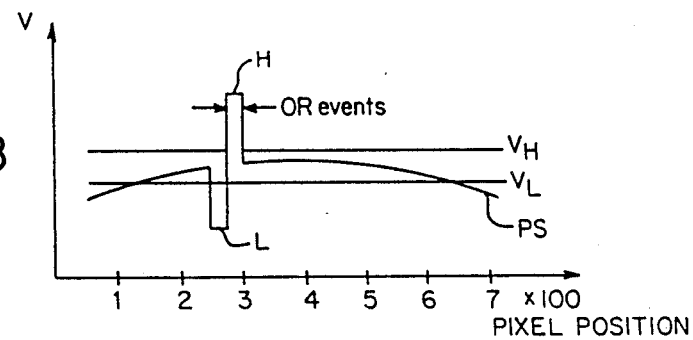

First, the high and low reference values, VRH and VRL, are all set to a predetermined maximum value to start with the broadest possible reference range having a high threshold VH and a low threshold VL as shown in FIG. 8A. Second, the overrange OR condition is enabled so that interrupt circuit 37 will provide an overrange OR interrupts, I3. Third, signal processor 14 causes sheet material 2 to be scanned several times and provides any overrange OR interrupts, I3, to histogram circuit 32 which collects the characteristic signals CS and the interrupt signals I. Fourth, if no overrange OR interrupts, I3, occur as shown in FIG. 8A, the intensity of light source 5 is increased if not already at its maximum value or the scan speed of the photosites of camera 12 is reduced to increase exposure time if the intensity of light source 5 is already at its maximum value. If overrange OR interrupts, I3, have occurred as shown in FIG. 8B, the intensity of light source 5 is reduced if it has been set to a value greater than its minimum intensity or the scan speed of the photosites of camera 12 is increased if the intensity of light source 5 is already set at the minimum value. Whether or not overrange OR interrupt. I3, occurs can be determined during the converter access mode when the characteristic signals CS are stored in computer 30 which can be programmed so that histogram circuit 32 generates a histogram of the occurrences of the states of the characteristic signals CS it has collected as shown in FIG. 9.

This procedure adjusts the dynamic range of the magnitude of the pixel signal PS with respect to the reference ranges being used to normalize the variations in the system as described above. For example, with respect to variations in the surface of sheet material 2, a black printed line 7 absorbing light and a highly reflective printed line 6 on sheet material 2 are shown in FIG. 1. The black line 7 would generate pixel signals PS having relatively low magnitudes as shown at L and the reflective line 6 would generate pixel signals PS having relatively high magnitudes as shown at H. Thus, the dynamic range of the pixel signals PS can be adjusted to use the full reference range as shown in FIG. 8A.

Figure 8C:
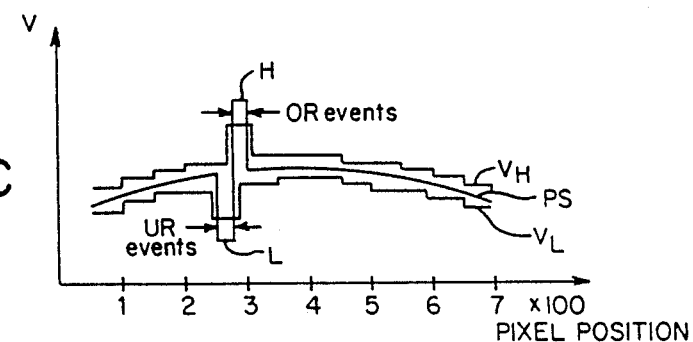
Figure 8D:
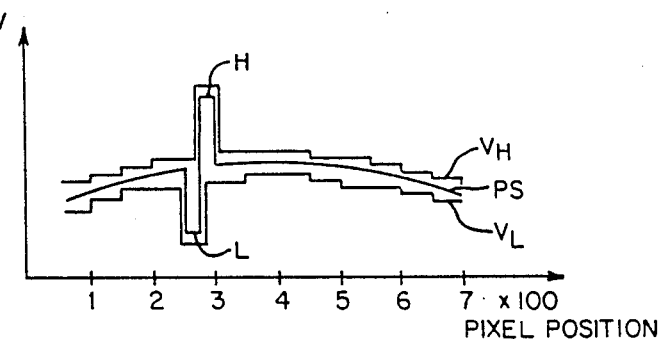

Once the dynamic range of the pixel signals has been adjusted within the maximum reference range, the individual reference ranges for each pixel signal can be separately adjusted as follows and as shown in FIGS. 8C and 8D. First, the high and low reference values, VRH and VRL, are set at some "perceived" value. Second, both the overrange OR and underrange UR conditions are enabled by setting the IS1 and IS2 signals low as described above. Third, signal processor 14 scans the photosites of camera 12 several times and transmits the characteristic signals CS and corresponding address signals to converter memory 64 and any interrupt signals, overrange I3 or underrange I1, to histogram circuit 32.

Computer 30 averages the data signals DS received for each pixel position, the number of data signals DS being equal to the number of scans taken, to obtain a properly standardized data signal reference value for each pixel position. Computer 30 generates the high reference value VRH for each pixel signal by adding a predetermined number, high factor, to the average data signal value and generates the low reference value VRL by subtracting a predetermined number, low factor, from the same average data signal value for that pixel position. For example, if the average data signal value were $8_{10}$ ($1000_2$) and the high and low factors were 2 and 1, respectively, the high reference value VRH would be $10_{10}$ ($1010_2$) and the low reference value VRL would be $7_{10}$ ($0111_2$). These values would then be stored in reference memory 44 as described above and would define the reference range for that pixel position as having a specific high threshold VH and low threshold VL. Computer 30 performs the same computation for each pixel position to generate the ranges as shown in FIG. 8C.

It should be noted that overrange and underrange interrupt, I1 and I3, events may still occur as shown in 8C because "average" data signal values were used to compute the high and low reference values, VRH and VRL. Such interrupts are accumulated in histogram circuit 32 which generates a histogram of the interrupt signals as shown in FIG. 10. The histogram shows the number of occurrences of interrupts at each pixel position and, in this example, clearly indicates that the printed lines 6, 7 are still generating overrange and underrange interrupt, I1 and I3. Thus, computer 30 is programmed to further adjust the high and low reference values, VRH and VRL, at those pixel positions to further widen the reference range around the high and low pixel signals. H and L. as shown in FIG. 8D. Thus, the printing variations are effectively normalized so that signal processor 14 generates interrupt signals I indicating real flaws in sheet material 2 such as a repeating mark 8 and or a streak 9 as shown in FIGS. 1 and 10.

This procedure also normalizes the variations in the intensity of the source of light 5, or the sensitivity of the photosites. For example, the intensity of the light is greater in the middle of sheet material 2 than at its edges as indicated by the curved line representing the magnitude of the pixel signals PS shown in FIGS. 8A-8D, the high and low reference values. VRH and VRL, are adjusted at each pixel position and essentially follow the curved line as shown in FIG. 8C. This procedure can also be used during the actual inspection mode to detect slow process variations, such as for example a gradual variation in the reflectance of the sheet material due to changes in the raw material being used, and adjusting the high and low reference values. VRH and VRL, to accommodate the gradual variations without disturbing the on-going inspection process. In the inspection mode, computer 30 is programmed so that bit 5 of control output 3, the reference memory access signal, goes low and is provided to timer 79 to commence processing and disable write access to reference memory 44. Computer 30 is also programmed so that bit 6 of control output 3 provides a low signal at output C7 to enable the inverted output-enable input OE so that the high and low reference values, VRH and VRL, are read from reference memory 44. The low signal at bit 6 is also provided at the inverting input of gate 78 so that the high and low reference values. VRH and VRL, are transmitted from reference memory 44 to DACs 48 and 50 via bus 45 through latch 46 and buses 47 and 49. respectively. In the present embodiment, the high and low reference values, VRH and VRL are stored as a single word in reference memory 44, reference value DV, and split by latch 46 into the separate 4-bit words previously described. The TIMER 3 signal at output C6 clocks latch 6 such that the high and low reference values, VRH and VRL, are presented to DACS 48. 50 at the proper time. Referring more specifically to FIGS. 3 and 4, the noninverting output of flip-flop 94 stays high because bit of control output 3 is held low to disable flip-flop 4. Thus, the TIMER 1 signal is enabled to clock reference address counter 42.

Controller 36 is also used to generate an end of scan signal EOS. To accomplish this, computer 30 is programmed so that control output 2 enables latch 72a to transfer a number corresponding to the last address position of the scan from the system data bus 34 to comparator 72b which is connected to the reference address counter 42 by bus 43. When reference address counter 42 up to equal that number, an end of scan signal EOS is provided to the toggle input of flip flop 80, the second input of AND gate 71, the third input of gate 73, and to the camera 12 as output C9 from controller 36. Control output 1 enables the end of scan EOS signal to reset reference address counter 42 via output C10.

In the interrupt mode, which can function simultaneously with the other modes, controller 36 comprises interruption select circuitry, shown in FIG. 2 and referred to above, which provides interrupt select signals IS enabling interrupt circuit 37 to generate any one of the four interrupt signals I described above. An "auto switch" mode can also be used during the interrupt mode to automatically switch interrupt circuit 37 from one condition to the inverted condition in order to detect the edges of flaws in the sheet material. For example, when the auto switch mode is engaged, interrupt circuit 37 initially may be enabled for an overrange condition and then enabled for the not overrange condition after an overrange interrupt, I3, is generated. When a not overrange interrupt,, I4, is generated, interrupt circuit 37 is again switched and enabled for the overrange condition as shown in FIG. 11. The auto switch mode is turned off for the overrange and underrange conditions when bits 2 and 1, respectively, from latch 76 are set low and provided to the corresponding JK inputs of flip-flops 86 and 90, respectively. The operation of the auto switch mode will be discussed below in more detail.

Assuming that the auto switch mode is turned off, the four interrupt select signals IS are provided as follows. When the EOS signal goes low, and computer 30 is programmed so that control outputs 3 and 4 are also low. output of gate 73 also goes low and is provided to one input of each of gates 83, 85, 87 and 89. The EOS signal will be switched through any one or combination of these gates that is enabled by its other input. The overrange and not overrange conditions are selected when computer 30 is programmed so that bit 3 of latch 74 goes low so that the IS2 signal at output C2 is low. The overrange condition is enabled when computer 30 is programmed so that bit 2 of latch 74 goes low and enables the output of gate 83 to clear flip flop 86 so that the IS3 signal at output C3 goes low. When IS2 and IS3 are low, gate 103 of interrupt circuit 37 is enabled to provide an overrange interrupt I3 when $Q_4$ goes high. The not overrange condition is enabled when computer 30 is programmed so that bit 2 of latch 74 goes hiqh and enables the output of gate 85 to set flip-flop 86 so that the IS4 signal at output C3 goes high. When IS2 is low and IS3 is high, gate 104 of interrupt circuit 37 is enabled to generate a not overrange interrupt I4 when $Q_4$ is low.

Correspondingly, the underrange and not underrange conditions are selected when computer 30 is programmed so that bit 4 of latch 74 goes low so that the ISI signal at output C1 is low. The underrange condition is enabled when computer 30 is programmed so that bit 1 of latch 74 goes low and enables the output of gate 87 to clear flip-flop 90 so that the IS4 signal at output C4 goes low. When ISI and IS4 are both low, gate 101 of interrupt circuit 37 is enabled to provide an underrange interrupt I1 when $Q_0$ to $Q_4$ are all low. The not overrange condition is enabled when computer 30 is programmed so that bit 1 of latch 74 goes high and enables the output of gate 89 to set flip flop 90 so that the IS4 at output C4 goes high. When ISI is low and IS4 is high, gate 102 of interrupt circuit 37 is enabled to generate a not underrange interrupt I2 when all of the signals, $Q_0$ to $Q_4$ are not low.

When the auto switch is turned on, the interrupt circuitry just described operates in the same fashion, except that it switches between interrupt conditions in response to the auto switch as described above. The auto switch will commence switching from any one of the interrupt conditions that has already been enabled so that the auto switch starts at a known state. The auto switch is used to toggle between the overrange and not overrange conditions as follows. When computer 30 is programmed so that bit 2 of latch 76 goes high, flip flop 86 is placed in the toggling mode and will change states in response to a negative-going edge of a toggling signal. A negative going edge is provided after an overrange interrupt. I3, is provided by interrupt circuit 37 and causes flip flop 86 to change states so that the IS3 signal at output C3 goes high which enables interrupt circuit 37 for a not overrange condition. Correspondingly, another negative-going edge is provided after a not overrange interrupt, I4, is generated which causes flip flop 86 to change states so that the IS3 signal at output C3 goes low and enables the overrange condition of interrupt circuit 37 as described above.

The auto switch is also used to toggle between the underrange and not underrange condition in a similar fashion. When computer 30 is programmed so that bit 1 of latch 76 goes high, flip flop 90 is placed in the toggling mode and will change state in response to a negative-going edge of the toggling signal. A negative-going edge is provided after an underrange interrupt. I1, is provided by circuit 37 and causes flip flop 90 to change state so that the IS4 signal at output C4 goes high which enables interrupt circuit 37 for a not underrange condition. Correspondingly, another negative-going edge is provided after a not overrange interrupt, I2, is generated which causes flip flop 90 to change states so that the IS4 signal at output C4 goes low and enables the underrange condition of interrupt circuit 37 as described above.

The toggling signal is provided by a toggling timer comprising time delay device 92 and gates 91 and 93. Referring to FIGS. 2 and 6, the toggling timer operates as follows. In the present embodiment, output T1 provides the TIMER 1 signal which is approximately 50 nanoseconds. The output of one-shot multivibrator 56 provides a pulse of short duration after the negative-going edge of the TIMER 1 signal. If any interrupts I occur for a pixel signal PS being converted by quantizer 40. e.g., an overrange OR interrupt signal I3, an AINT signal is generated when the output of gate 105 goes low a short period of time T2 after the corresponding conversion by quantizer 40. The circuitry comprising time delay device 92 and gates 91 and 93 is used to delay the TIMER 1 signal by enough time, T3, about 30 nanoseconds in the present embodiment, to ensure that the AINT signal has time to settle and that histogram circuit 32 has enough time to latch the interrupt signals I.

When the delayed TIMER 1 signal goes low, it is summed at gate 93 with the low AINT signal to provide a low output from gate 93. When the inverted TIMER 1 signal goes low, it is summed at gate 91 with the low output from 93 to provide he neqative-going edge of the toggling signal from the output of gate 91 to the toggle inputs of flip flops 86 and 90 as described above. As a result, the interrupt select signal IS3 goes high to enable interrupt circuit 37 for the not overrange condition as also described above. When the delayed TIMER 1 signal goes high, the outputs of gates 91 and 93 go high to effectively reset the toggle signal for the next pixel signal PS to be converted and to be ready for another interrupt signal I if one occurs. The AINT signal goes high at a later point in time if no interrupt signal I occurs as a result of the next pixel signal PS being converted. Thus, the negative-going edge of the toggling signal is provided after a not overrange interrupt signal I4 to change the state of flip-flop 86, so that interrupt circuit 37 is again enabled for an overrange condition as shown in FIG. 6.

As described above and shown in FIG. 11, the auto switch circuit is used to identify the edges of defects or flaws so that the shape of the defect is known and can even be displayed as shown in FIG. 12. With this information, the amount of "significant" data that needs to be stored is further reduced because the overrange or underrange interrupt signals, I1 and I3, that occur between the edges do not need to be stored; this makes the inspection process even more efficient. A defect D is illustrated as it would appear on sheet material 2. Assuming that the auto switch is initialized for an overrange condition, interrupt circuit 37 would generate an overrange interrupt signal I3 at pixel position 65 on scan line 85. Interrupt circuit 37 would then be switched for a not overrange condition and would generate a not interrupt signal I4 at pixel position 85 on scan line 85. Correspondingly, interrupt circuit 37 would identify the edge points at each scan line to effectively provide an outline of the defect D. Depending on the resolution of camera 12, and the relative size of the defects being detected, the auto switch can be used to provide a very precise digital outline of any defects.

Having described the invention in detail and by reference to preferred embodiments thereof, it will be apparent that other modifications and variations are possible without departing from the scope of the invention to find in the appended claims.

What is claimed is:

1. Apparatus for inspecting sheet material having known characteristics, said apparatus comprising:
   means for providing a plurality of pixel signals, each having a magnitude representing the intensity of electromagnetic radiation received from a corresponding point on the sheet material;
   signal processing means, responsive to said means for providing a plurality of pixel signals, for comparing the magnitude of each one of said pixel signals to a corresponding reference range defined by the known characteristics of the sheet material for each one of said pixel signals and generating a characteristic signal made up of an event signal for each of said magnitudes falling outside of said corresponding reference range and a data signal for each of said magnitudes falling within said reference range, said at a signal representing the magnitude of said pixel signal, and an address signal representing the point on the sheet material for which said characteristic signal is generated; and
   system processing means, responsive to said signal processing means, for storing said event signals and said corresponding address signals to provided an indication of deviation from the known characteristics of the sheet material.

2. Apparatus as recited in claim 1, wherein said means for providing a plurality of pixel signals includes an array of photosites, each providing one of said pixel signals.

3. Apparatus as recited in claim 2, wherein said address signals each represent the position of a photosite in said a ray corresponding to the location of the point on the sheet material at which said characteristic signal is generated.

4. Apparatus as recited in claim 3, wherein the length of said array corresponds to the width of the sheet material so that said photosites provide successive sets of pixel signals, each set corresponding to a scan of the width of the sheet material.

5. Apparatus as recited in claim 4, wherein said signal processing means includes control means, responsive to said system processing means, for providing an end-of-scan signal when said array provides a full set of pixel signals, and wherein said system processing means, responsive to said end-of-scan signals, provides a histogram of the occurrences of said event signals at each photosite position for a predetermined number of scans.

6. Apparatus as recited in claim 1, wherein said data signals are n-bit digital signals and wherein said system processing means provides a histogram of the occurrences of the states of said n-bit digital signals.

7. Apparatus as recited in claim 1, wherein said signal processing means includes reference means, responsive to said system processing means, for storing a high and a low reference value for each of said reference ranges, said high and low reference values being derived in response to measured values of the known characteristics of the sheet material and being provided to define each of said reference ranges between a high threshold and a low threshold for comparison to the magnitude of said pixel signals.

8. Apparatus as recited in claim 7, wherein said signal processing means further includes converter means, responsive to said system processing means, for reading and storing said data signals and said corresponding address signals, said system processing means reading said signals from said converter means, adding a high factor to each of said data signals to determine said high reference value, subtracting a low factor from each of said data signals to determine said corresponding low reference value, and storing said high and low reference values in said reference means for defining said reference ranges for comparison to the magnitudes of said pixel signals.

9. Apparatus as recited in claim 8, wherein said means for providing a plurality of pixel signals includes an array of photosites, each providing one of said pixel signals and wherein said address signals each represent the position of a photosite in said array corresponding to the location of the point on the sheet material at which said characteristic signal is generated.

10. Apparatus as recited in claim 9, wherein the length of said array corresponds to the width of the sheet material so that said photosites provide successive sets of pixel signals, each set corresponding to a scan of the width of the sheet material.

11. Apparatus as recited in claim 10, wherein said signal processing means includes control means, responsive to said system processing means, for providing an end-of-scan signal when said array provides a full set of pixel signals, and wherein said system processing means, responsive to said end-of-scan signal, provides updated reference ranges for comparison tot he magnitudes of pixel signals at each photosite position.

12. Apparatus as recited in claim 7, wherein said signal processing means further includes control means, responsive to said system processing means, for providing an overrange interrupt signal when said event signal is generated because the magnitude of said pixel signal is greater than said high threshold.

13. Apparatus as recited in claim 7, wherein said signal processing means further includes control means responsive to said system processing means, for generating a not overrange interrupt signal when the magnitude of said pixel signal is less than said high threshold.

14. Apparatus as recited in claim 7, wherein said signal processing means further includes control means, responsive to said system processing means, for providing an overrange interrupt signal when the magnitude of said pixel signal is greater than said high threshold and then switching to generate a not overrange interrupt signal when the magnitude of said pixel signal is less than said high threshold.

15. Apparatus as recited in claim 14, wherein said means for providing a plurality of pixel signals includes an array of photosites, each providing one of said pixel signals and wherein said address signals each represent the position of a photosite in said array corresponding to the location of the point on the sheet material at which said characteristic signal is generated.

16. Apparatus as recited in claim 15, wherein the length of said array corresponds to the width of the sheet material so that said photosites provide successive sets of pixel signals, each set corresponding to a scan of the width of the sheet material.

17. Apparatus as recited in claim 16, wherein said signal processing means includes control means, responsive to said system processing means, for providing an end-of-scan signal when said array provides a full set of pixel signals, and wherein said system processing means. responsive to said end-of-scan signals, provides a histogram of the occurrences of said overrange and not overrange interrupt signals at each photosite position for a predetermined number of scans.

18. Apparatus as recited in claim 7, wherein said signal processing means further includes control means. responsive to said system processing means, for proViding an underrange interrupt signal when said event signal is generated because the magnitude of said pixel signal is less than said low threshold.

19. Apparatus as recited in claim 7, wherein said signal processing means further includes control means responsive to said system processing means, for generating a not underrange interrupt signal when the magnitude of said pixel signal is greater than said low threshold.

20. Apparatus as recited in claim 7, wherein said signal processing means further includes control means. responsive to said system processing means, for providing an underrange interrupt signal when the magnitude of said pixel signal is less than said low threshold and then switching to generate a not underrange interrupt signal when the magnitude of said pixel signal is greater than said low threshold.

21. Apparatus as recited in claim 20, wherein said means for providing a plurality of pixel signals includes an array of photosites, each providing one of said pixel signals and wherein said address signals each represent the position of a photosite in said array corresponding to the location of the point on the sheet material at which said characteristic signal is generated.

22. Apparatus as recited in claim 21, wherein the length of said array corresponds to the width of the sheet material so that said photosites provide successive sets of pixel signals, each set corresponding to a scan of the width of the sheet material.

23. Apparatus as recited in claim 22, wherein said signal processing means includes control means, responsive to said system processing means, for providing an end-of-scan signal when said array provides a full set of pixel signals, and wherein said system processing means. responsive to said end-of-scan signals, provides a histogram of the occurrences of said underrange and not underrange interrupt signals at each photosite position for a predetermined number of scans.

24. Apparatus as recited in claim 1, wherein said means for providing a plurality of pixel signals includes an array of photosites, successive pairs of said photosites each providing one of said pixel signals.

25. Apparatus as recited in claim 24, wherein the magnitude of each of said pixel signals is the sum of the signals provided by each photosite of said pair.

26. Apparatus as recited in claim 24, wherein the magnitude of each of said pixel signals is the sum of the sum of the signals provided by each photosite of said pair and the difference between the signals provided by each photosite of said pair.

27. Apparatus as recited in claim 24, wherein said address signals each represent the position of a pair of said photosites in said a ray corresponding to the location of the point on the sheet material for which said characteristic signal is generated.

28. Apparatus for inspecting sheet material having known characteristics, said apparatus comprising:
  means for providing a plurality of pixel signals each having a magnitude representing the intensity of electromagnetic radiation received from a corresponding point on the sheet material;
  signal processing means, responsive to said means for providing a plurality of pixel signals, for comparing the magnitude of each one of said pixel signals to a corresponding reference range defined by the known characteristics of the sheet material for each one of said pixel signals and generating a data signal for each of said magnitudes falling within its corresponding reference range, said data signal representing he magnitude of said pixel signal, and an address signal representing the point on the sheet material for which said data signal is generated and storing said data signals and corresponding address signals; and
  system processing means, responsive to said signal processing means, for storing said data signals and the corresponding address signals.

29. Apparatus as recited in claim 28, wherein said signal processing means includes reference mans, responsive to said system processing means, for storing a high and a low reference value for each of said reference ranges, said high and low reference values being derived in response to measured values of the known characteristics of the sheet material and being provided to define each of said reference ranges between a high threshold and a low threshold for comparison to the magnitude of said pixel signals.

30. Apparatus as recited in claim 29, wherein said system processing means reads said data and address signals from said signal processing means, adds a high factor to each of said data signals to determine said high reference value, subtracts a low factor from each of said data signals to determine said corresponding low reference value, and stores said high and low reference values in said reference means for defining reference ranges for comparison to the magnitude of pixel signals.

31. Apparatus as recited in claim 30, wherein said means for providing a plurality of pixel signals includes an array of photosites, each providing one of said pixel signals and wherein said address signals each represent the position of a photosite in said array corresponding to the location of the point on the sheet material at which said data signal is generated.

32. Apparatus as recited in claim 31, wherein the length of said array corresponds to the width of the sheet material so that said photosites provide successive sets of pixel signals, each set corresponding to a scan of the width of the sheet material.

33. A method for inspecting sheet material having known characteristics, comprising the steps of:
  providing a plurality of pixel signals, each having a magnitude representing the intensity of electromagnetic radiation received from a corresponding point on the sheet material for each one of said pixel signals;
  comparing the magnitude of each one of said pixel signals to a corresponding reference range defined by the known characteristics of the sheet material;
  generating a characteristic signal made up on an event signal for each of the magnitudes falling outside of the corresponding reference range and a data signal for each of the magnitudes falling within the range, the data signal representing the magnitude of the pixel signal;
  generating an address signal representing the point on the sheet material for which the characteristic signal is generated; and
  storing the event signals and the corresponding address signals to provided an indication of deviation from the known characteristics of the sheet material.

34. A method as recited in claim 33, wherein the plurality of pixel signals is provided by an array of photosites, each providing one of the pixel signals and wherein the address signals each represent the position of a photosite in the array corresponding to the location of the point on the sheet material for which the characteristic signal is generated.

35. A method as recited in claim 34, wherein the length of the array corresponds to the width of the sheet material so that the photosites provide successive sets of pixel signals, each set corresponding to a scan of the width of the sheet material.

36. A method as recited in claim 35, further comprising steps of providing an end-of-scan signal when the array provides a full set of pixel signals, and, in response to the end-of-scan signal, providing a updated reference ranges for comparison to the magnitude of pixel signals generated at each photosite position.

37. A method as recited in claim 33, further comprising steps of storing the data signals as n-bit digital signals and providing a histogram of the occurrences of the state of the n-bit digital signals.

38. A method as recited in claim 33, further comprising steps of deriving a high and a low reference value for each of said reference ranges in response to measure values of the known characteristics of the sheet material, storing said high and low reference values and providing said high and low reference values to define each of said reference range between a high threshold and a low threshold for comparison to the magnitude of the pixel signals.

39. A method as recited in claim 38, further comprising steps of storing the data signals and the corresponding address signals, adding a high factor to each of the data signals to determining the high reference value, subtracting a low factor from each of the data signals to determine the corresponding low reference value, and storing the high and low reference values thus obtained to define reference ranges for comparison to the magnitude of pixel signals.

40. A method as recited in claim 39, wherein the plurality of pixel signals is provided by an array of photosites, each providing one of said pixel signals and wherein the address signals each represent the position of a photosite in the array corresponding to the location of the point on the sheet material at which the characteristic signal is generated.

41. A method as recited in claim 40, wherein the length of said array corresponds to the width of the sheet material so that the photosites provide successive sets of pixel signals, each set corresponding to a scan of the width of the sheet material.

42. A method as recited in claim 41, further comprising steps of providing an end-of-scan signal when the array provides a full set of pixel signals, and, in response to the end-of-scan signal, providing updated reference ranges for comparison to the magnitude of subsequent pixel signals generated at each photosite position.

43. A method as recited in claim 38, further comprising the steps of providing an overrange interrupt signal when the magnitude of the pixel signal is greater than the high threshold and generating a not overrange interrupt signal when the magnitude of the pixel signal is less than the high threshold.

44. A method as recited in claim 38, further comprising the steps of providing an underrange interrupt signal when the magnitude of a pixel signal is less than the low threshold and generating a not underrange interrupt signal when the magnitude of the pixel signal is greater than the low threshold.

45. A method for inspecting sheet materials having known characteristics, comprising the steps of:
 providing a plurality of pixel signals each having a magnitude representing the intensity of electromagnetic radiation received from a corresponding point on the sheet material;
 comparing the magnitude of each one of the pixel signals to a corresponding reference range defined by the known characteristics of the sheet material for each one of said pixel signals;
 generating a data signal for each of the magnitudes falling within the reference range, the data signal representing the magnitude of the pixel signal;
 generating a data signal for each of the magnitudes falling within the reference range, the data signal representing the magnitude of the pixel signal;
 generating an address signal representing the point on the sheet material for which the data signal is generated; and
 storing the data signals and corresponding address signals.

46. A method as recited in claim 45, further comprising steps of deriving a high and a low reference value for each of the reference ranges in response to measured values of the known characteristics of the sheet material, storing the high and low reference values and providing the high and low reference values to define each of the reference ranges between a high threshold and a low threshold for comparison to the magnitude of the pixel signals.

47. A method as recited in claim 46, further comprising the steps of storing the data and address signals, adding a high factor to each of the data signals to determined the high reference value, subtracting a low factor from each of the data signals to determined the corresponding low reference value, and storing the high and low reference values to define reference ranges for comparison to the magnitude of pixel signals.

48. A method as recited in claim 47, wherein the plurality of pixel signals is provided by an array of photosites, each providing one of the pixel signals and wherein the address signals each represent the position of a photosite in the array corresponding to the location of the point on the sheet material for which the data signal is generated.

49. A method as recited in claim 48, wherein the length of the array corresponds to the width of the sheet material so that the photosites provide successive sets of pixel signals, each set corresponding to a scan of the width of the sheet material.

* * * * *

UNITED STATES PATENT AND TRADEMARK OFFICE
CERTIFICATE OF CORRECTION

PATENT NO. : 4,950,911

DATED : August 21, 1990

INVENTOR(S) : Paul Williams et al

Page 1 of 4

It is certified that error appears in the above-identified patent and that said Letters Patent is hereby corrected as shown below:

Col. 3, Line 64, "onl" should be --only--.

Col. 4, Line 24, "-$I_4$. and" should be ---$I_4$, and--.

Col. 4, Line 53, "plastic." should be --plastic,--.
Col. 5, Line 12, "printing 6. 7" should be --printing 6, 7--.
Col. 5, Line 29, "photosite, provides" should be --photosite, n, provides--.
Col. 5, Line 49, "(not shown). one" should be --(not shown), one--.
Col. 6, Line 46, "signal $D_0$ where to $Q_4$ are all low." should be --signal DS where $Q_0$ to $Q_4$ are all low--.
Col. 6, Line 52, "where $Q_0$-$Q_4$ all low" should be --where $Q_0$-$Q_4$ are all low--.
Col. 6, Line 53, "underrange, UR. event." should be --underrange, UR, event.--.
Col. 6, Line 55, "MCI0319" should be --MC10319--.
Col. 7, Line 22, "DV.$DV_0$" should be --DV, $DV_0$--.
Col. 7, Line 24, "value. $DV_4$ to $DV_7$" should be --value, $DV_4$ to $DV_7$,--.
Col. 7, Line 24, "and 49." should be --and 49,--.
Col. 8, Line 17, "82a. the" should be --82a, the--.
Col. 8, Line 47, "connected t the" should be --connected to the--.
Col. 9, Line 32, "DV(4)." should be --DV(4),--.
Col. 9, Line 36, "CS, Q0 to Q4" should be --CS, $Q_0$ to $Q_4$--.
Col. 9, Line 61, "signal. Il. i.e.." should be --signal, Il, i.e.,--.
Col. 9, Line 66, "condition:" should be --condition;--.
Col. 10, Line 5, "i.e.." should be --i.e.,--.
Col. 10, Line 17, "OR" should be --OR--.
Col. 10, Line 31, "and. as" should be --and, as--.

UNITED STATES PATENT AND TRADEMARK OFFICE
CERTIFICATE OF CORRECTION

PATENT NO. : 4,950,911
DATED : August 21, 1990
INVENTOR(S) : Paul Williams et al It is certified that error appears in the above-identified patent and that said Letters Patent is hereby corrected as shown below:

```
Col. 10, Line 44,  "66. In" should be --66. (new paragraph)
                   In--.
Col. 10, Line 54,  "82bas" should be --82b as--.
Col. 10, Line 59,  "RA." should be --RA,--.
Col. 10, Line 63,  "values. VRH" should be --values, VRH--.
Col. 11, Line 9,   "the output" should be --the inverted output--.
Col. 11, Line 11,  "values. VRH" should be --values, VRH--.
Col. 11, Line 54,  "interrupt.I3," should be --interrupt, I3,--.
Col. 12, Line 54,  "signals. H and L. as" should be --signals, H
                   and L, as--.
Col. 12, Line 65,  "values. VRH" should be --values, VRH--.
Col. 13, Line 4,   "values. VRH" should be --values, VRH--.
Col. 13, Line 17,  "values. VRH" should be --values, VRH--.
Col. 13, Line 19,  "and 49. respectively" should be --and 49,
                   respectively--.
Col. 13, Line 25,  "latch 6 such" should be --latch 46 such--.
Col. 13, Line 26,  "DACS 48.50" should be --DACS 48, 50--.
Col. 13, Line 29,  "bit of control" should be --bit 5 of control--.
Col. 13, Line 30,  "flip-flop 4." should be --flip-flop 94.--.
Col. 13, Line 39,  "42 up to" should be --42 increments up to--.
Col. 13, Line 60,  "interrupt,," should be --interrupt,--.
Col. 14, Line 5,   "low. output" should be --low, the output--.
Col. 14, Line 28,  "ISI" should be --IS1--.
Col. 14, Line 32,  "ISI and 1S4" should be --IS1 and IS4--.
Col. 14, Line 38,  "IS4 at" should be --IS4 signal at--.
Col. 14, Line 55,  "interrupt. I3," should be --interrupt, I3,--.
Col. 15, Line 2,   "interrupt. I1," should be --interrupt, I1,--.
Col. 15, Line 3,   "provided by circuit 37" should be --provided
                   by interrupt circuit 37--.
Col. 15, Line 15,  "output Tl" should be --output T1--.
Col. 15, Line 21,  "40. e.g.," should be --40, e.g.,--.
Col. 13, Line 6,   "process. In" should be --process. (new paragraph)
                   In--.
```

UNITED STATES PATENT AND TRADEMARK OFFICE
CERTIFICATE OF CORRECTION

PATENT NO. : 4,950,911

DATED : August 21, 1990

INVENTOR(S) : Paul Williams et al

It is certified that error appears in the above-identified patent and that said Letters Patent is hereby corrected as shown below:

| | | |
|---|---|---|
| Col. 15, | Line 34, | "output from 93 to provide he negative-going" should be --output from gate 93 to provide the negative-going--. |
| Col. 15, | Lines 65 and 66 | "not interrupt" should be --not overrange interrupt--. |
| Col. 16, | Line 27, | "said at a signal" should be --said data signal--. |
| Col. 17, | Line 36, | "comparison tot he" should be --comparison to the--. |
| Col. 18, | Line 6, | "means. responsive" should be --means, responsive--. |
| Col. 18, | Line 6, | "signals" should be --signal--. |
| Col. 18, | Line 11, | "means." should be --means,--. |
| Col. 18, | Line 12, | "proViding" should be --providing--. |
| Col. 18, | Line 23, | "means." should be --means,--. |
| Col. 18, | Line 48, | "means. responsive to said end-of-scan signals," should be --means, responsive to said end-of-scan signal,--. |
| Col. 18, | Line 60 and 61 | "the sum of the sum of" should be --the summation of the sum of-- |
| Col. 19, | Line 15, | "representing he" should be --representing the--. |
| Col. 19, | Line 24, | "mans" should be --means--. |
| Col. 20, | Line 25, | "providing a updated" should be --providing updated--. |
| Col. 20, | Line 39, | "range" should be --ranges--. |
| Col. 20, | Line 63, | "claim 41" should be --claim 44--. |
| Col. 21, | Line 26, (claim 45, lines 14-16) | "remove lines 26, 27, and 28 - these lines duplicate the previous three lines." |

UNITED STATES PATENT AND TRADEMARK OFFICE
CERTIFICATE OF CORRECTION

PATENT NO. : 4,950,911
DATED : August 21, 1990
INVENTOR(S) : Paul Williams et al It is certified that error appears in the above-identified patent and that said Letters Patent is hereby corrected as shown below:

Col. 22, Line 14, "determined" should be --determine--.

Signed and Sealed this

Twenty-fifth Day of June, 1991

Attest:

HARRY F. MANBECK, JR.

Attesting Officer

Commissioner of Patents and Trademarks